(12) United States Patent
Daunert et al.

(10) Patent No.: US 8,465,981 B2
(45) Date of Patent: Jun. 18, 2013

(54) POLYPEPTIDES, SYSTEMS, AND METHODS USEFUL FOR DETECTING GLUCOSE

(75) Inventors: Sylvia Daunert, Coral Gables, FL (US); Kendrick Turner, Washington, DC (US); Smita Joel, Miami, FL (US); Laura Rowe, Harrodsburg, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 268 days.

(21) Appl. No.: 12/672,403

(22) PCT Filed: Aug. 6, 2008

(86) PCT No.: PCT/US2008/072354
§ 371 (c)(1),
(2), (4) Date: Feb. 1, 2011

(87) PCT Pub. No.: WO2009/021052
PCT Pub. Date: Feb. 12, 2009

(65) Prior Publication Data
US 2011/0117661 A1    May 19, 2011

Related U.S. Application Data

(60) Provisional application No. 60/954,269, filed on Aug. 6, 2007, provisional application No. 60/954,348, filed on Aug. 7, 2007.

(51) Int. Cl.
*G01N 33/66* (2006.01)
*G01N 33/68* (2006.01)
*G01N 33/50* (2006.01)
*G01N 21/76* (2006.01)
*C07K 14/00* (2006.01)

(52) U.S. Cl.
USPC ............. 436/95; 436/56; 436/63; 436/86; 436/89; 436/164; 436/172; 422/82.05; 422/82.08; 435/14; 530/350

(58) Field of Classification Search
USPC ............ 436/56, 63, 86, 89, 95, 164, 166, 436/172; 422/82.05, 82.08; 435/6.1, 14; 530/350; 600/365
See application file for complete search history.

(56) References Cited

U.S. PATENT DOCUMENTS

| | | |
|---|---|---|
| 4,703,756 A | 11/1987 | Gough et al. |
| 5,001,054 A | 3/1991 | Wagner |
| 5,165,407 A | 11/1992 | Wilson et al. |
| 5,342,789 A | 8/1994 | Chick et al. |
| 6,197,534 B1 | 3/2001 | Lakowicz et al. |
| 6,231,733 B1 | 5/2001 | Nilsson et al. |
| 6,239,255 B1 | 5/2001 | Furlong et al. |
| 6,277,627 B1 | 8/2001 | Hellinga |
| 6,432,723 B1 | 8/2002 | Plaxco et al. |
| 6,521,446 B2 | 2/2003 | Hellinga |
| 6,855,556 B2 | 2/2005 | Amiss et al. |
| 6,977,180 B2 | 12/2005 | Hellinga et al. |
| 7,064,103 B2 | 6/2006 | Pitner et al. |
| 7,146,203 B2 | 12/2006 | Botvinick et al. |
| 7,163,511 B2 | 1/2007 | Conn et al. |
| 7,169,600 B2 | 1/2007 | Hoss et al. |
| 7,183,068 B2 | 2/2007 | Burson et al. |
| 7,256,038 B2 | 8/2007 | Daugherty et al. |
| 7,629,172 B2 * | 12/2009 | Alarcon et al. ............... 436/95 |
| 7,851,593 B2 * | 12/2010 | Hsieh et al. ............... 530/350 |
| 2001/0039350 A1 * | 11/2001 | Thorwart et al. ........... 548/128 |
| 2002/0004217 A1 | 1/2002 | Hellinga |
| 2003/0018438 A1 * | 1/2003 | Nestor et al. ............... 702/27 |
| 2003/0130167 A1 | 7/2003 | Pitner et al. |
| 2003/0134346 A1 | 7/2003 | Amiss et al. |
| 2003/0153026 A1 | 8/2003 | Alarcon et al. |
| 2003/0232383 A1 | 12/2003 | Daunert et al. |
| 2004/0118681 A1 | 6/2004 | Hellinga et al. |
| 2005/0014290 A1 | 1/2005 | Hsieh et al. |
| 2005/0042704 A1 | 2/2005 | Alarcon et al. |
| 2005/0148003 A1 * | 7/2005 | Keith et al. ............... 435/6 |
| 2006/0216752 A1 | 9/2006 | Pitner et al. |
| 2006/0216753 A1 | 9/2006 | Pitner et al. |
| 2006/0280652 A1 | 12/2006 | Pitner et al. |
| 2007/0136825 A1 | 6/2007 | Frommer et al. |
| 2007/0161047 A1 | 7/2007 | Zhong et al. |
| 2008/0044856 A1 * | 2/2008 | Amiss et al. ............... 435/69.1 |

FOREIGN PATENT DOCUMENTS

WO    2004101769    11/2004

OTHER PUBLICATIONS

Salins et al. In Chemical and Biological Sensors for Environmental Monitoring, ACS Symposium Series, American Chemical Society: Washington, DC, Chapter 6, pp. 87-101, Aug. 15, 2000.*

Siegrist, et al.; Continuous glucose sensor using novel genetically engineered binding polypeptides towards in vivo applications; Sensors and Actuators; B 149; 2010; pp. 51-58.

* cited by examiner

*Primary Examiner* — Maureen Wallenhorst
(74) *Attorney, Agent, or Firm* — Stites & Harbison PLLC; Mandy Wilson Decker

(57) ABSTRACT

The presently-disclosed subject matter provides biosensors for detecting molecules of interest. The biosensors include a polypeptide capable of selectively-binding glucose, wherein the polypeptide molecule is selected from: an unnatural analogue of wild type glucose binding protein; a fragment of wild type glucose binding protein; and an unnatural analogue fragment of wild type glucose binding protein.

22 Claims, 6 Drawing Sheets

POLYPEPTIDES, SYSTEMS, AND METHODS USEFUL FOR DETECTING GLUCOSE

RELATED APPLICATIONS

This application claims priority from U.S. Provisional Application Ser. Nos. 60/954,269 filed on Aug. 6, 2007, and 60/954,348 filed on Aug. 7, 2007, the entire disclosures of which are incorporated herein by this reference.

TECHNICAL FIELD

The presently-disclosed subject matter relates to biosensors, and systems and methods useful for detecting glucose.

BACKGROUND

Monitoring blood glucose levels in a diabetic individual is important for maintaining metabolic control in the individual. Currently-available systems and methods of monitoring glucose levels require extraction of blood from the diabetic individual at multiple times during each day, e.g., finger prick. As such, only information about blood glucose levels at discrete time points is made available. Additionally, extracting blood for use in testing can be painful, and as a result, can lead to low compliance or non-compliance by diabetic individuals.

Efforts have therefore been made to develop an effective system and method for monitoring blood glucose levels in a continuous and less invasive manner. Biosensors have been proposed for use in the in vivo, continuous detection of blood analyte levels. A biosensor includes an element capable of specifically detecting an analyte of interest, allowing a measurable signal to be produced, which can be correlated to analyte concentration.

Biosensors for detecting glucose can include an element that selectively binds glucose. For example, wild type glucose binding protein (wtGBP) is capable of binding glucose. GBP of *Escherichia coli* is a 33 kDa periplasmic binding protein. GBP consists of two distinctly similarly folded globular domains that are connected to each other by three peptide segments. The sugar binding site is located in the cleft of the protein formed between the two domains. The binding of glucose is accompanied by a conformational change of the protein at the hinge region. In the open form of GBP (in the absence of glucose) the two domains are far apart and the cleft is exposed to the solvent, while in the closed form the glucose is engulfed in the cleft.

Although biosensors have made use of certain wtGBPs, such biosensors have drawbacks. For example, GBPs are not very stable at room temperature. As such, there are apparent problems associated biosensors that make use of wtGBP for monitoring blood glucose levels in diabetic patients. Furthermore, currently-available systems and methods for continuously-detecting glucose are associated with a significant inability to detect glucose levels in the hypoglycemic ranges in a reliable manner. Further, these available systems also suffer from short lifespans and are not easily used for routine clinical use. In addition, the use of current wtGBPs for continuous blood glucose monitoring for implantable or catheter-based devices is complicated by the need for sterilization. The development of novel proteins with improved thermal and chemical stability will lead to easier and more cost-effective means of sterilization.

Accordingly, there is a need in the art for systems and methods for detecting glucose levels in a subject in a continuous manner, at ambient temperatures, with operability for clinical use, reliability, specificity, and sensitivity.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter provides, in some embodiments, a biosensor for detecting a molecule of interest. In some embodiments, the biosensor comprises an isolated polypeptide molecule capable of selectively-binding glucose. In some embodiments, the polypeptide molecule is selected from: an unnatural analogue of wild type glucose binding protein; a fragment of wild type glucose binding protein; and an unnatural analogue fragment of wild type glucose binding protein. The biosensor further comprises a label associated with the polypeptide molecule, wherein binding of glucose to the polypeptide molecule causes the label to generate a signal, such that the glucose can be detected.

In some embodiments, the polypeptide molecule is a fragment of wild type glucose binding protein. In some embodiments, the polypeptide molecule is a fragment of the amino acid sequence of SEQ ID NO: 1, wherein up to about 13 amino acids are truncated from the N-terminus and/or wherein up to about 83 amino acids are truncated from the C-terminus of SEQ ID NO: 1. In some embodiments, the polypeptide molecule is a fragment of the amino acid sequence of SEQ ID NO: 5, wherein up to about 12 amino acids are truncated from the N-terminus and/or wherein about 99 amino acids are truncated from the C-terminus of SEQ ID NO: 5. In some embodiments, the polypeptide molecule, comprises the amino acid sequence of SEQ ID NOs: 1-7.

In some embodiments, the polypeptide molecule is an unnatural analogue of wild type glucose binding protein, wherein one or more natural amino acids of wild type glucose binding protein are replaced with one or more unnatural amino acids. In some embodiments, the one or more natural amino acids of wild type glucose binding protein are replaced with one or more unnatural amino acids as set forth in Table A. In some embodiments, the polypeptide molecule is an unnatural analogue or an unnatural analogue fragment, wherein one or more natural leucines are replaced with unnatural leucines. In some embodiments, one or more natural leucines are replaced with 5,5,5-trifluoroleucine. In some embodiments, one or more natural leucines are replaced with 5,5,5-trifluoro-DL-leucine. In some embodiments, one or more natural tryptophans are replaced with 5-fluorotryptophan. In some embodiments, one or more natural tryptophans are replaced with 5-fluoro-L-tryptophan.

In some embodiments, the polypeptide molecule is stable over a wider range of temperatures relative to wtGBP. In some embodiments, the polypeptide molecule is stable at temperatures between about 55° C. and about 75° C.

In some embodiments, the label is a fluorophore. In some embodiments, label is the fluorophore MDCC. In some embodiments, binding of glucose to the polypeptide molecule causes the label to generate a detectably altered fluorescence intensity of the fluorophore such that the glucose can be detected. In some embodiments, the fluorescence intensity can be correlated to the concentration of the glucose in a sample.

In some embodiments, the label is attached to an amino acid site of the polypeptide molecule selected from Asp 13, Asp 44, Val 68, Ala 71, Phe 90, Lys 92, Glu 93, Pro 94, Lys 97, Gly 109, Thr 110, Asp 111, Gly 151, Pro 153, Ala 155, Asp 184, Asp 212, Leu 255, Ala 258, Asn 260, Ala 262, Arg 292, Val 293, and Pro 294.

In some embodiments of the presently-disclosed subject matter, a method for detecting a glucose molecule is provided. In some embodiments, the method comprises contacting a biosensor disclosed herein with a sample of interest; detecting the signal; and collecting and displaying the signal with a detection and data collection device, to thereby detect the glucose. In some embodiments, the glucose is continuously detected.

BRIEF DESCRIPTION OF THE SEQUENCE LISTING

Figures 1A, 1B, 1C, 1D:
FIG. 1A is a rendering of the three-dimensional structure of the polypeptide of SEQ ID NO: 1. The 3D structures were created using a protein structure modeling program called DS Viewer Pro. Structural information for proteins is available online through the RCSB Protein Data Bank. This structural information is available in the form of a file that contains the coordinates in three dimensions for proteins such as they have been published in current literature sources. Protein structure files are available by PDB#. In this document, the PDB files used are as follows: #1GLG (wtGBP from *E. coli*) and #2H3H (wtGBP from *T. maritima*), FIG. 1A and FIG. 2A, respectively.
FIG. 1B is a rendering of the three-dimensional structure of the polypeptide of SEQ ID NO: 2. The structure shown is a truncated form of the complete wtGBP from *E. coli* shown in FIG. 1A, in which the dark gray portion represents the structure of the truncated form specified by the figure and the light gray portion represents the portion of the wtGBP that is being omitted.
FIG. 1C is a rendering of the three-dimensional structure of the polypeptide of SEQ ID NO: 3. The structure shown is a truncated form of the complete wtGBP from *E. coli* shown in FIG. 1A, in which the dark gray portion represents the structure of the truncated form specified by the figure and the light gray portion represents the portion of the wtGBP that is being omitted.
FIG. 1D is a rendering of the three-dimensional structure of the polypeptide of SEQ ID NO: 4. The structure shown is a truncated form of the complete wtGBP from *E. coli* shown in FIG. 1A, in which the dark gray portion represents the structure of the truncated form specified by the figure and the light gray portion represents the portion of the wtGBP that is being omitted.

SEQ ID NO: 1 includes an amino acid sequence for wild type glucose binding protein (wtGBP) from *Escherichia coli* (GenBank Accession number X05646). The disclosed sequence provided is without the N-terminal signaling peptide.

SEQ ID NO: 2 includes an amino acid sequence for tGBP1, including amino acids 14-296 of SEQ ID NO: 1.

SEQ ID NO: 3 includes an amino acid sequence for tGBP2, including amino acids 14-256 of SEQ ID NO: 1.

SEQ ID NO: 4 includes an amino acid sequence for tGBP3, including amino acids 14-226 of SEQ ID NO: 1.

SEQ ID NO: 5 includes an amino acid sequence for wild type glucose binding protein (wtGBP) from *Thermotoga maritima* (GenBank® Accession No. NP_227930), where the first 31 amino acids making up the N-terminal signaling peptide have been removed.

SEQ ID NO: 6 includes an amino acid sequence for tGRP4, including amino acids 13-253 of SEQ ID NO: 5.

SEQ ID NO: 7 includes an amino acid sequence for tGRP5, including amino acids 13-205 of SEQ ID NO: 5.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein.

While the following terms are believed to be well understood by one of ordinary skill in the art, the following definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently-disclosed subject matter includes isolated polypeptides useful for detecting glucose. The presently-disclosed subject matter further includes biosensors, systems, and methods for detecting glucose.

The presently-disclosed subject matter includes isolated polypeptide molecules that are capable of selectively-binding glucose, and biosensors that include isolated polypeptide molecules that are capable of selectively-binding glucose. In some embodiments, the isolated polypeptide molecule is a fragment of a wild type glucose binding protein (wtGBP). In some embodiments, the isolated polypeptide molecule is an unnatural analogue of wtGBP. In some embodiments, the isolated polypeptide molecule is an unnatural analogue fragment of wtGBP.

The terms "polypeptide," "protein," and "peptide," which are used interchangeably herein, refer to a polymer of the 20 protein amino acids, including modified amino acids (e.g., phosphorylated, glycated, etc.) and amino acid analogs, regardless of size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins, and fragments of proteins, unless otherwise noted. The terms "protein", "polypeptide", and "peptide" are used interchangeably herein when referring to a gene product and fragments thereof. Thus, exemplary polypeptides include gene products, naturally occurring proteins, homologs, orthologs, paralogs, fragments, and other equivalents, variants, fragments, and analogs of the foregoing. In some embodiments, the term polypeptide includes a conservatively substituted variant.

The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

The term "isolated," when used in the context of an isolated polypeptide, is a polypeptide that, by the hand of man, exists apart from its native environment and is therefore not a product of nature.

As used herein, the term "selectively-bind" refers to an interaction between glucose and a binding site of a polypeptide molecule. In some embodiments, the interaction between glucose and the binding site can be identified as "selective" if: the equilibrium dissociation constant ($K_d$) is about the same or less than the $K_d$ of glucose and a reference polypeptide binding site; the equilibrium inhibitor dissociation constant ($K_i$) is about the same or less than the $K_i$ of glucose and a reference polypeptide binding site; or the effective concentration at which binding of glucose is inhibited by 50% ($EC_{50}$) is about the same or less than the $EC_{50}$ of glucose and a reference polypeptide binding site. For example, glucose selectively binds an isolated polypeptide molecule that is a fragment, unnatural analogue, or unnatural analogue fragment of wild type Glucose Binding Protein (wtGBP) if the $K_d$, $K_i$, and/or $EC_{50}$ is about the same or less than the $K_d$ of glucose and wtGBP.

In some embodiments, the interaction between glucose and the binding site can be identified as "selective" when the equilibrium dissociation constant ($K_d$) is less than about 100 nM, 75 nM, 50 nM, 25 nM, 20 nM, 10 nM, 5 nM, or 2 nM. In some embodiments, the interaction between glucose and the binding site can be identified as "selective" when the equilibrium inhibitor dissociation constant ($K_i$) is less than about is less than about 100 µM, 75 µM, 50 µM, 25 µM, 20 µM, 10 µM, 5 µM, or 2 µM, when competing with glucose. In some embodiments, the interaction between glucose and the binding site can be identified as "selective" when the effective concentration at which glucose binding is inhibited by 50% ($EC_{50}$) is less than about 500 µM, 400 µM, 300 µM, 100 µM, 50 µM, 25 µM, or 10 µM.

The terms "polypeptide fragment" or "fragment", when used in reference to a polypeptide, refers to a polypeptide in which amino acid residues are absent as compared to the full-length reference polypeptide itself, but where the remaining amino acid sequence is usually identical to the corresponding positions in the reference polypeptide. Such deletions can occur at the amino-terminus or carboxy-terminus of the reference polypeptide, or alternatively both. A fragment can retain one or more of the biological activities of the reference polypeptide. In some embodiments, a fragment can comprise a domain or feature, and optionally additional amino acids on one or both sides of the domain or feature, which additional amino acids can number from 5, 10, 15, 20, or more residues.

As used herein, the term "unnatural analogue" refers to a polypeptide wherein one or more natural amino acids are replaced with unnatural amino acids, relative to a reference polypeptide. Examples of unnatural amino acids are set forth in Table A, provided herein below.

As used herein, the term "unnatural analogue fragment" refers to a polypeptide fragment wherein one or more natural amino acids are replaced with unnatural amino acids, relative to a reference polypeptide.

As used herein, wtGBP refers to a reference protein including the amino acid residues of a full-length wild type glucose binding protein. A full-length wild type glucose binding protein will be known to those of ordinary skill in the art. Some embodiments of the polypeptide molecule of the presently-disclosed subject matter can be described with reference to the amino acid residues of a wtGBP. In some embodiments, the wtGBP can be a full-length wtGBP from *E. coli* (GenBank® Accession No. X05646). In some embodiments, the wtGBP can be the polypeptide of SEQ ID NO: 1. In some embodiments, the wtGBP can be a full-length wtGBP from *T. maritima* (GenBank® Accession No. NP_227930). In some embodiments, the wtGBP can be the polypeptide of SEQ ID NO: 5. In some embodiments, the wtGBP can be a full-length wtGBP from *Thermus thermophilus* (GenBank® Accession No. YP_004303).

In some embodiments of the presently-disclosed subject matter, the isolated polypeptide molecule is a fragment of wtGBP that selectively binds glucose. For example, in some embodiments, the polypeptide molecule comprises a fragment of wtGBP from *E. coli* including amino acids 14-296, set forth in SEQ ID NO: 2 (referred to herein as tGBP1). For another example, in some embodiments, the polypeptide molecule comprises a fragment of wtGBP from *E. coli* including amino acids 14-256, set forth in SEQ ID NO: 3 (referred to herein as tGBP2). For yet another example, in some embodiments, the polypeptide molecule comprises a fragment of wtGBP from *E. coli* including amino acids 14-226, set forth in SEQ ID NO: 4 (referred to herein as tGBP3). For another example, in some embodiments, the polypeptide molecule comprises a fragment of wtGBP from *T. maritima* including amino acids 13-253, set forth in SEQ ID NO: 6 (referred to herein as tGBP4). For another example, in some embodiments, the polypeptide molecule comprises a fragment of wtGBP from *T. maritima* including amino acids 13-205, set forth in SEQ ID NO: 7 (referred to herein as tGBP5).

Figures 2A, 2B, 2C:
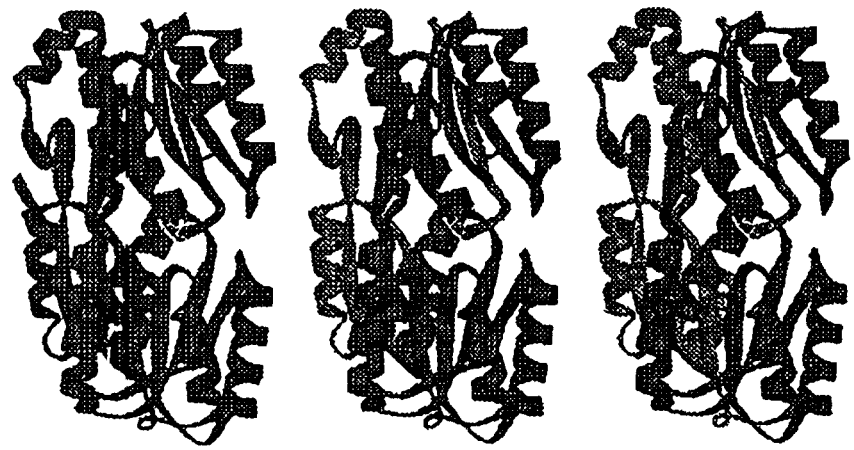
FIG. 2A is a rendering of the three-dimensional structure of the polypeptide of SEQ ID NO: 5. The 3D structures were created using DS Viewer Pro.
FIG. 2B is a rendering of the three-dimensional structure of the polypeptide of SEQ ID NO: 6. The structure shown is a truncated form of the complete wtGBP from *T. maritime* shown in FIG. 2A, in which the dark gray portion represents the structure of the truncated form specified by the figure and the light gray portion represents the portion of the wtGBP that is being omitted.
FIG. 2C is a rendering of the three-dimensional structure of the polypeptide of SEQ ID NO: 7. The structure shown is a truncated form of the complete wtGBP from *T. maritime* shown in FIG. 2A, in which the dark gray portion represents the structure of the truncated form specified by the figure and the light gray portion represents the portion of the wtGBP that is being omitted.

It is contemplated that isolated polypeptide molecules of the presently-disclosed subject matter can be fragments and/or unnatural analogues of wtGBP for various species, or an isolated polypeptide molecule having a three-dimensional structure that is sufficiently similar to such a wtGBP or functional fragment thereof, such that it is capable of specifically binding glucose. Three-dimensional structures of the isolated polypeptide molecules of SEQ ID NOS: 1-7 are provided in FIGS. 1A-2C. These 3D structures were created using a protein structure modeling program called DS Viewer Pro. Structural information for proteins is available online through the RCSB Protein Data Bank. This structural information is available in the form of a file that contains the coordinates in three dimensions for proteins such as they have been published in current literature sources. Protein structure files are available by PDB#. In the present context, the PDB files used are as follows: #1GLG (wtGBP from *E. coli*) and #2H3H (wtGBP from *T. maritima*). These structures are shown in FIG. 1A and FIG. 2A respectively. Structures shown in FIG. 1B, FIG. 1C, and FIG. 1D are truncated forms of the complete wtGBP from *E. coli* shown in FIG. 1A in which the dark gray portion represents the structure of the truncated form specified by that figure and the light gray portion represents the portion of the wtGBP that is being omitted. Likewise, FIG. 2B and FIG. 2C represent truncated forms of the complete wtGBP from *T. maritime* shown in FIG. 2A in which the dark gray portion represents the structure of the truncated form specified by that figure and the light gray portion represents the portion of the wtGBP that is being omitted.

In some embodiments, the polypeptide molecule of the presently-disclosed subject matter comprises a fragment of wtGBP, wherein up to 1, 2, 3, 4, 5, 6, 7, 8, 9, 10, 11, 12, 13, 14, 15, 16, 17, 18, 19, 20, 21, 22, 23, 24, or 25 amino acids are truncated from the N-terminus of the wtGBP. In some embodiments, the polypeptide molecule comprises a fragment of wtGBP, wherein up to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 amino acids are truncated from the C-terminus of wtGBP.

Without wishing to be bound by theory, it is believed that certain amino acids are useful for enhancing functionality of fragments of wtBGP provided from particular species. For example, amino acids 14, 91, 152, 158, 211, 236, and 256 of wtGBP from *E. coli* (SEQ ID NO: 1) are believed to be involved in the binding of glucose. As such, in some embodiments, the isolated polypeptide molecule is a fragment of wtGBP from *E. coli* (SEQ ID NO: 1) that includes amino acids 14, 91, 152, 158, 211, 236, and 256. In some embodiments, the isolated polypeptide molecule is a fragment of wtGBP from *E. coli* (SEQ ID NO: 1) that includes at least 1, 2, 3, 4, 5, or 6 of the amino acids selected from amino acids 14, 91, 152, 158, 211, 236, and 256. Similarly, amino acid 13 of wtGBP from *T. maritima* (SEQ ID NO: 5) is believed to be involved in the binding of glucose. As such, in some embodiments, the isolated polypeptide molecule is a fragment of wtGBP from *T. maritima* (SEQ ID NO: 5) that includes amino acid 13.

In some embodiments of the presently-disclosed subject matter, the isolated polypeptide molecule is an unnatural analogue of wtGBP. For example, in some embodiments, the polypeptide molecule comprises the sequence of wtGBP, wherein one or more natural amino acids are replaced with one or more unnatural amino acids set forth in Table A. In some embodiments, the wtGBP can be from *E. coli*. In some embodiments, the wtGBP can be from *T. maritima*. In some embodiments, the wtGBP can be from *T. thermophilus*.

TABLE A

| Natural Amino Acid | Unnatural Amino Acid | Structure of Unnatural Amino Acid |
|---|---|---|
| Alanine | 2-Pyridylalanine | |
| Alanine | 3-Pyridylalanine | |
| Alanine | 4-Pyridylalanine | |
| Alanine | p-Iodophenylalanine | |
| Alanine | p-Bromophenylalanine | |

TABLE A-continued

| Natural Amino Acid | Unnatural Amino Acid | Structure of Unnatural Amino Acid |
|---|---|---|
| Alanine | L-2-Aminobutyric acid | |
| Glycine | L-Allylglycine | |
| Glycine | L-Propargylglycine | |
| Glycine | 2-Methoxy-phenylglycine | |
| Glycine | 3-Thienylglycine | |
| Leucine | 5,5,5-trifluoro-DL-leucine | |
| Lysine | D-Lysine | $H_2NCH_2(CH_2)_2CH_2C$—$C$—$OH$ |
| Phenylalanine | Alpha-methyl-L-phenylalanine | |
| Phenylalanine | p-Amino-DL-phenylalanine | $H_2N$—⌬—$CH_2CH$—$C$—$OH$ · $xH_2O$ |

TABLE A-continued
| Natural Amino Acid | Unnatural Amino Acid | Structure of Unnatural Amino Acid |
|---|---|---|
| Proline | Alpha-Benzyl-proline-HCl | 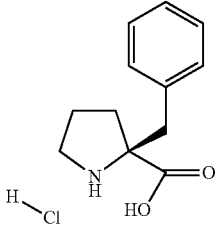 [SMILES: Cl ; O=C(O)[C@@]1(Cc2ccccc2)CCCN1] |
| Proline | Gamma-(3-fluoro-benzyl)-L-proline-HCl | 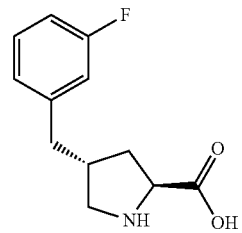 [SMILES: O=C(O)[C@@H]1C[C@@H](Cc2cccc(F)c2)CN1] |
| Tryptophan | 5-Hydroxy-L-tryptophan | 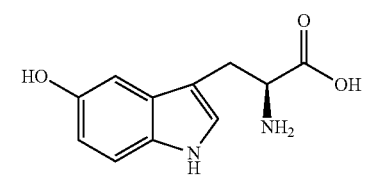 [SMILES: N[C@@H](Cc1c[nH]c2ccc(O)cc12)C(=O)O] |
| Tryptophan | 5-fluoro-L-tryptophan | 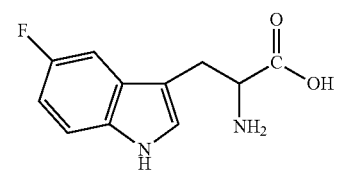 [SMILES: NC(Cc1c[nH]c2ccc(F)cc12)C(=O)O] |
| Tryptophan | 7-Azatryptophan | 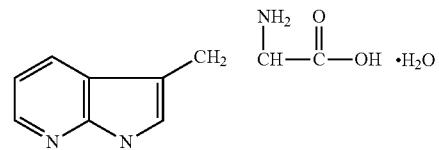 |
| Tryptophan | 6-Azatryptophan | 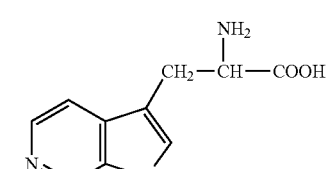 |
| Tryptophan | 4-Aminotryptophan | 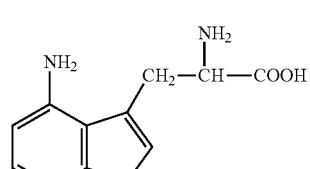 |
| Tryptophan | 5-Aminotryptophan | 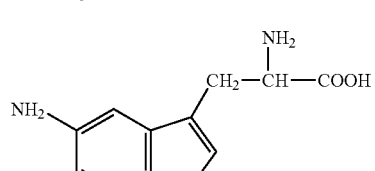 |

TABLE A-continued

| Natural Amino Acid | Unnatural Amino Acid | Structure of Unnatural Amino Acid |
|---|---|---|
| Tyrosine | 3-Fluoro-L-tyrosine | 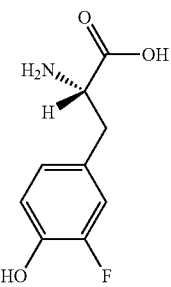 [SMILES: N[C@@H](Cc1ccc(O)c(F)c1)C(=O)O] |
| Valine | D-Norvaline | 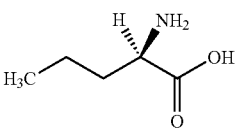 |

In some embodiments, the polypeptide molecule comprises the sequence of a fragment of wtGBP, wherein one or more natural amino acids are replaced with one or more unnatural amino acids set forth in Table A. In some embodiments, the wtGBP can be from *E. coli*. In some embodiments, the wtGBP can be from *T. maritima*. In some embodiments, the wtGBP can be from *T. thermophilus*. In some embodiments, the polypeptide molecule comprises the sequence of SEQ ID NO: 1, wherein one or more natural amino acids are replaced with one or more unnatural amino acids set forth in Table A. In some embodiments, the polypeptide molecule comprises the sequence of SEQ ID NO: 2, wherein one or more natural amino acids are replaced with one or more unnatural amino acids set forth in Table A. In some embodiments, the polypeptide molecule comprises the sequence of SEQ ID NO: 3, wherein one or more natural amino acids are replaced with one or more unnatural amino acids set forth in Table A. In some embodiments, the polypeptide molecule comprises the sequence of SEQ ID NO: 4, wherein one or more natural amino acids are replaced with one or more unnatural amino acids set forth in Table A. In some embodiments, the polypeptide molecule comprises the sequence of SEQ ID NO: 5, wherein one or more natural amino acids are replaced with one or more unnatural amino acids set forth in Table A. In some embodiments, the polypeptide molecule comprises the sequence of SEQ ID NO: 6, wherein one or more natural amino acids are replaced with one or more unnatural amino acids set forth in Table A. In some embodiments, the polypeptide molecule comprises the sequence of SEQ ID NO: 7, wherein one or more natural amino acids are replaced with one or more unnatural amino acids set forth in Table A.

In some embodiments of the presently-disclosed subject matter, the isolated polypeptide molecule is an unnatural analogue of wtGBP, including one or more of the following substitutions:

(i) at least one alanine is replaced with an unnatural alanine;
(ii) at least one glycine is replaced with an unnatural glycine;
(iii) at least one lysine is replaced with an unnatural lysine;
(iv) at least one phenylalanine is replaced with an unnatural phenylalanine;
(v) at least one proline is replaced with an unnatural proline;
(vi) at least one tyrosine is replaced with an unnatural tyrosine;
(vii) at lest one valine is replaced with an unnatural valine;
(viii) at least one leucine is replaced with an unnatural leucine; and
(ix) at least one tryptophan is replaced with an unnatural tryptophan.

In some embodiment, at least one alanine is replaced with an unnatural alanine selected from: 2-Pyridylalanine, 3-Pyridylalanine, 4-Pyridylalanine, p-Iodophenylalanine, p-Bromophenylalanine, and L-2-Aminobutyric acid.

In some embodiment, at least one glycine is replaced with an unnatural glycine selected from: L-Allylglycine, L-Propargylglycine, 2-Methoxy-phenylglycine, and 3-Thienylglycine.

In some embodiments, at least one lysine is replaced with D-lysine.

In some embodiments, at least one phenylalanine is replaced with an unnatural phenylalanine selected from: Alpha-methyl-L-phenylalanine, and p-Amino-DL-phenylalanine In some embodiments, at least one proline is replaced with an unnatural proline selected from: alpha-Benzyl-proline-HCl, and gamma-(3-fluoro-benzyl)-L-proline-HCl.

In some embodiments, at least one tyrosine is replaced with 3-Fluoro-L-tyrosine.

In some embodiments, at least one valine is replaced with D-norvaline.

In some embodiments, at least one leucine is replaced with 5,5,5-trifluoro-DL-leucine.

In some embodiments, at least one tryptophan is replaced with an unnatural tryptophan selected from: 5-Hydroxy-L-tryptophan, 5-fluoro-L-tryptophan, 7-azatryptophan, 6-azatryptophan, and amino tryptophans.

In some embodiments, the polypeptide molecule is a wtGBP or fragment thereof, wherein one or more natural leucines are replaced with unnatural leucines. Without wishing to be bound by theory, it is believed that replacing one or more natural leucines with unnatural leucines confers enhanced thermal and chemical stability to the resulting polypeptide analogue. In some embodiments, all natural leucines are replaced with unnatural leucines. In some embodiments, the unnatural leucines are 5,5,5-trifluoro-DL-leucine.

In some embodiments, the polypeptide molecule comprises the sequence of SEQ ID NO: 1, wherein one or more natural leucines are replaced with unnatural leucines. In some embodiments, the polypeptide molecule comprises the sequence of SEQ ID NO: 1, wherein one or more natural leucines are replaced with 5,5,5-trifluoro-DL-leucine. In some embodiments, the polypeptide molecule comprises the sequence of SEQ ID NO: 1, wherein all of the natural leucines are replaced with 5,5,5-trifluoro-DL-leucine.

In some embodiments, the polypeptide molecule comprises the sequence of SEQ ID NO: 2, wherein one or more natural leucines are replaced with unnatural leucines. In some embodiments, the polypeptide molecule comprises the sequence of SEQ ID NO: 2, wherein one or more natural leucines are replaced with 5,5,5-trifluoro-DL-leucine. In some embodiments, the polypeptide molecule comprises the sequence of SEQ ID NO: 2, wherein all of the natural leucines are replaced with 5,5,5-trifluoro-DL-leucine.

In some embodiments, the polypeptide molecule comprises the sequence of SEQ ID NO: 3, wherein one or more natural leucines are replaced with an unnatural leucines. In some embodiments, the polypeptide molecule comprises the sequence of SEQ ID NO: 3, wherein one or more natural leucines are replaced with 5,5,5-trifluoro-DL-leucine. In some embodiments, the polypeptide molecule comprises the sequence of SEQ ID NO: 3, wherein all of the natural leucines are replaced with 5,5,5-trifluoro-DL-leucine.

In some embodiments, the polypeptide molecule comprises the sequence of SEQ ID NO: 4, wherein one or more natural leucines are replaced with an unnatural leucines. In some embodiments, the polypeptide molecule comprises the sequence of SEQ ID NO: 4, wherein one or more natural leucines are replaced with 5,5,5-trifluoro-DL-leucine. In some embodiments, the polypeptide molecule comprises the sequence of SEQ ID NO: 4, wherein all of the natural leucines are replaced with 5,5,5-trifluoro-DL-leucine.

In some embodiments, the polypeptide molecule comprises the sequence of SEQ ID NO: 5, wherein one or more natural leucines are replaced with an unnatural leucines. In some embodiments, the polypeptide molecule comprises the sequence of SEQ ID NO: 5, wherein one or more natural leucines are replaced with 5,5,5-trifluoro-DL-leucine. In some embodiments, the polypeptide molecule comprises the sequence of SEQ ID NO: 5, wherein all of the natural leucines are replaced with 5,5,5-trifluoro-DL-leucine.

In some embodiments, the polypeptide molecule comprises the sequence of SEQ ID NO: 6, wherein one or more natural leucines are replaced with unnatural leucines. In some embodiments, the polypeptide molecule comprises the sequence of SEQ ID NO: 6, wherein one or more natural leucines are replaced with 5,5,5-trifluoro-DL-leucine. In some embodiments, the polypeptide molecule comprises the sequence of SEQ ID NO: 6, wherein all of the natural leucines are replaced with 5,5,5-trifluoro-DL-leucine.

In some embodiments, the polypeptide molecule comprises the sequence of SEQ ID NO: 7, wherein one or more natural leucines are replaced with unnatural leucines. In some embodiments, the polypeptide molecule comprises the sequence of SEQ ID NO: 7, wherein one or more natural leucines are replaced with 5,5,5-trifluoro-DL-leucine. In some embodiments, the polypeptide molecule comprises the sequence of SEQ ID NO: 7, wherein all of the natural leucines are replaced with 5,5,5-trifluoro-DL-leucine.

Figure 12:
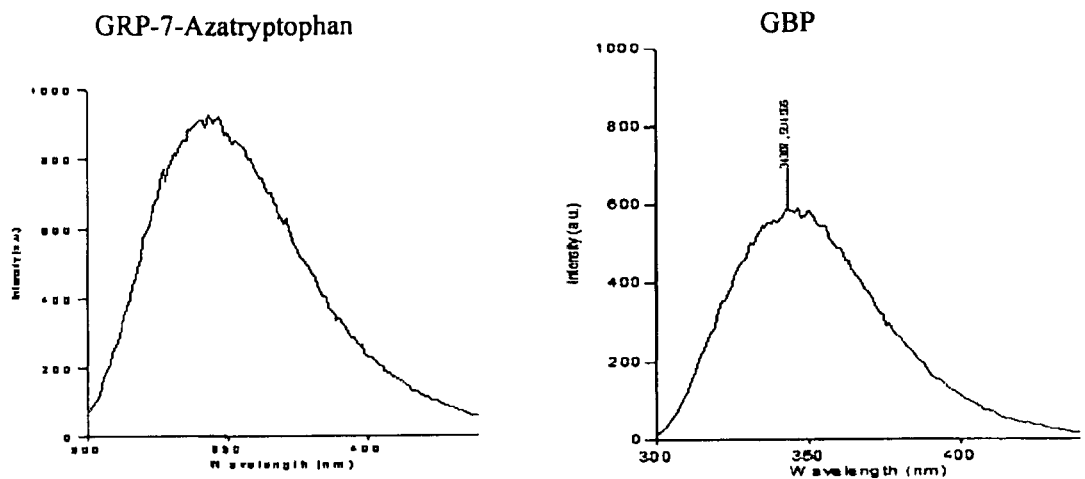
FIG. 12 are two graphs showing a comparison of the fluorescence emission intensity of GBP and GRP-7-Azatryptophan.
Figure 13:
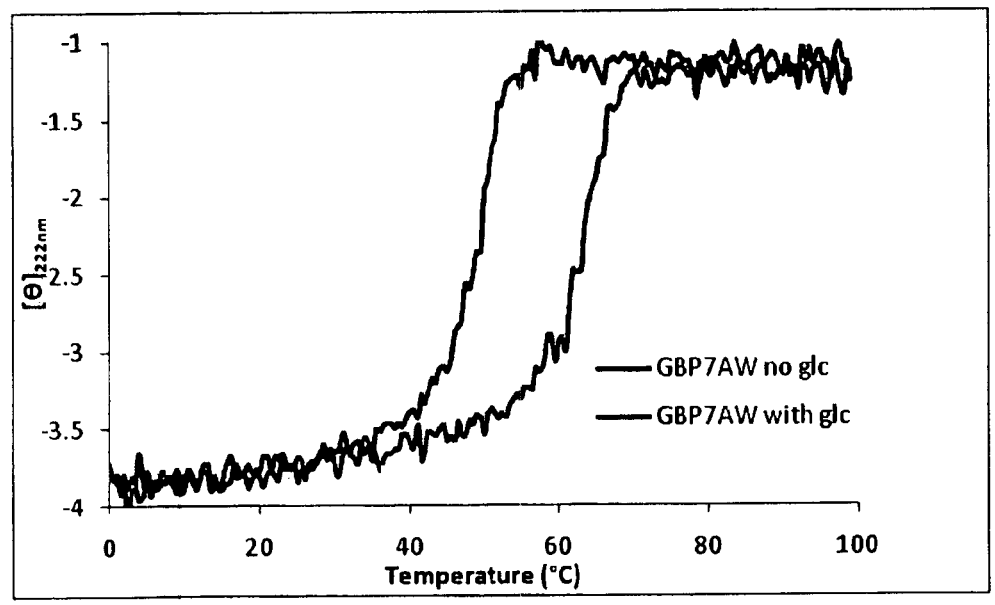
FIG. 13 is a CD spectrum showing a comparison of the fluorescence emission intensity over a range of temperatures of GRP-7-Azatryptophan without (light grey line) or with (dark grey line, shifted right toward higher temperature) bound glucose.

In some embodiments, the polypeptide molecule is a wtGBP or fragment thereof, wherein one or more natural tryptophans are replaced with unnatural tryptophans. Without wishing to be bound by theory, and with reference to the description herein of biomarkers including an isolated polypeptide molecule that is capable of emitting a signal when binding glucose, it is believed that replacing one or more natural tryptophans with unnatural tryptophans confers an enhanced ability of the resulting biomarker to emit a signal, e.g., fluoresce. For example, as shown in FIG. 12, the incorporation of 7-Azatryptophan in GRP enhances the intensity of fluorescence emission. Further, as shown in FIG. 13 the incorporation of 7-Azatryptophan in GRP results in a clearly distinguishable fluorescence signature between 7-Azatryptophan GRP with and without bound glucose across different temperatures. In some embodiments all natural tryptophans are replaced with unnatural tryptophans. In some embodiments, unnatural tryptophans are selected from: 5-hydroxy-L-tryptophan, and 5-fluoro-L-tryptophan. In some embodiments, the unnatural tryptophans are 5-fluorotryptophan.

In some embodiments, the polypeptide molecule comprises the sequence of SEQ ID NO: 1, wherein one or more natural tryptophans are replaced with unnatural tryptophans. In some embodiments, the polypeptide molecule comprises the sequence of SEQ ID NO: 1, wherein one or more natural tryptophans are replaced with unnatural tryptophan selected from: 5-hydroxy-L-tryptophan, and 5-fluoro-L-tryptophan. In some embodiments, the polypeptide molecule comprises the sequence of SEQ ID NO: 1, wherein one or more natural tryptophans are replaced with 5-fluorotryptophan. In some embodiments, the polypeptide molecule comprises the sequence of SEQ ID NO: 1, wherein all of the natural tryptophans are replaced with 5-fluorotryptophan.

In some embodiments, the polypeptide molecule comprises the sequence of SEQ ID NO: 2, wherein one or more natural tryptophans are replaced with unnatural tryptophans. In some embodiments, the polypeptide molecule comprises the sequence of SEQ ID NO: 2, wherein one or more natural tryptophans are replaced with unnatural tryptophan selected from: 5-hydroxy-L-tryptophan, and 5-fluoro-L-tryptophan. In some embodiments, the polypeptide molecule comprises the sequence of SEQ ID NO: 2, wherein one or more natural tryptophans are replaced with 5-fluorotryptophan. In some embodiments, the polypeptide molecule comprises the sequence of SEQ ID NO: 2, wherein all of the natural tryptophans are replaced with 5-fluorotryptophan.

In some embodiments, the polypeptide molecule comprises the sequence of SEQ ID NO: 3, wherein one or more natural tryptophans are replaced with unnatural tryptophans. In some embodiments, the polypeptide molecule comprises the sequence of SEQ ID NO: 3, wherein one or more natural tryptophans are replaced with unnatural tryptophan selected from: 5-hydroxy-L-tryptophan, and 5-fluoro-L-tryptophan. In some embodiments, the polypeptide molecule comprises the sequence of SEQ ID NO: 3, wherein one or more natural tryptophans are replaced with 5-fluorotryptophan. In some embodiments, the polypeptide molecule comprises the sequence of SEQ ID NO: 3, wherein all of the natural tryptophans are replaced with 5-fluorotryptophan.

In some embodiments, the polypeptide molecule comprises the sequence of SEQ ID NO: 4, wherein one or more natural tryptophans are replaced with unnatural tryptophans. In some embodiments, the polypeptide molecule comprises the sequence of SEQ ID NO: 4, wherein one or more natural tryptophans are replaced with unnatural tryptophan selected from: 5-hydroxy-L-tryptophan, and 5-fluoro-L-tryptophan. In some embodiments, the polypeptide molecule comprises the sequence of SEQ ID NO: 4, wherein one or more natural tryptophans are replaced with 5-fluorotryptophan. In some embodiments, the polypeptide molecule comprises the sequence of SEQ ID NO: 4, wherein all of the natural tryptophans are replaced with 5-fluorotryptophan.

In some embodiments, the polypeptide molecule comprises the sequence of SEQ ID NO: 5, wherein one or more natural tryptophans are replaced with unnatural tryptophans. In some embodiments, the polypeptide molecule comprises the sequence of SEQ ID NO: 5, wherein one or more natural tryptophans are replaced with unnatural tryptophan selected from: 5-hydroxy-L-tryptophan, and 5-fluoro-L-tryptophan. In some embodiments, the polypeptide molecule comprises the sequence of SEQ ID NO: 5, wherein one or more natural tryptophans are replaced with 5-fluorotryptophan. In some embodiments, the polypeptide molecule comprises the sequence of SEQ ID NO: 5, wherein all of the natural tryptophans are replaced with 5-fluorotryptophan.

In some embodiments, the polypeptide molecule comprises the sequence of SEQ ID NO: 6, wherein one or more natural tryptophans are replaced with unnatural tryptophans. In some embodiments, the polypeptide molecule comprises the sequence of SEQ ID NO: 6, wherein one or more natural tryptophans are replaced with unnatural tryptophan selected from: 5-hydroxy-L-tryptophan, and 5-fluoro-L-tryptophan. In some embodiments, the polypeptide molecule comprises the sequence of SEQ ID NO: 6, wherein one or more natural tryptophans are replaced with 5-fluorotryptophan. In some embodiments, the polypeptide molecule comprises the sequence of SEQ ID NO: 6, wherein all of the natural tryptophans are replaced with 5-fluorotryptophan.

In some embodiments, the polypeptide molecule comprises the sequence of SEQ ID NO: 7, wherein one or more natural tryptophans are replaced with unnatural tryptophans. In some embodiments, the polypeptide molecule comprises the sequence of SEQ ID NO: 7, wherein one or more natural tryptophans are replaced with unnatural tryptophan selected from: 5-hydroxy-L-tryptophan, and 5-fluoro-L-tryptophan. In some embodiments, the polypeptide molecule comprises the sequence of SEQ ID NO: 7, wherein one or more natural tryptophans are replaced with 5-fluorotryptophan. In some embodiments, the polypeptide molecule comprises the sequence of SEQ ID NO: 7, wherein all of the natural tryptophans are replaced with 5-fluorotryptophan.

In some embodiments, the polypeptide molecule comprises a wtGBP or fragment thereof, wherein at least one natural leucine is replaced with 5,5,5-trifluoro-DL-leucine, and at least one natural tryptophan is replaced with an unnatural tryptophan selected from 5-hydroxy-L-tryptophan, and 5-fluoro-L-tryptophan. In some embodiments, at least one natural leucine is replaced with 5,5,5-trifluoro-DL-leucine, and at least one natural tryptophan is replaced with 5-fluoro-L-tryptophan. In some embodiments, all natural leucines are replaced with 5,5,5-trifluoro-DL-leucine, and all natural tryptophans are replaced with 5-fluoro-L-tryptophan.

In some embodiments, when more than one of a particular natural amino acid is replaced with an unnatural amino acid, different unnatural amino acids can be used. For one example, in some embodiments, an unnatural analogue can include a first natural tryptophan replaced with 5-hydroxy-L-tryptophan, and a second natural tryptophan replaced with 5-fluoro-L-tryptophan.

In some embodiments of the presently-disclosed subject matter, the isolated polypeptide molecule is an unnatural analogue fragment of wtGBP that selectively binds glucose. In embodiments where the polypeptide molecule comprises an unnatural analogue fragment of wtGBP, natural amino acids can be replaced with unnatural amino acids, as described above with reference to unnatural analogues of wtGBP. In some embodiments, the polypeptide molecule comprises a fragment of wtGBP, wherein at least one natural amino acid is replaced with an unnatural amino acid, such as an unnatural amino acid set forth in Table A. For another example, in some embodiments, the polypeptide molecule comprises a fragment of SEQ ID NOs: 2, 3, 4, 5, 6, or 7, wherein at least one natural amino acid is replaced with an unnatural amino acid, such as an unnatural amino acid set forth in Table A. For another example, in some embodiments, the polypeptide molecule comprises a fragment of wtGBP wherein at least one leucine is replaced with 5,5,5-trifluoro-DL-leucine, and/or at least one tryptophan is replaced with 5-fluoro-L-tryptophan. In some embodiments, the polypeptide molecule comprises a fragment of wtGBP wherein all natural leucines are replaced with 5,5,5-trifluoro-DL-leucine, and/or all natural tryptophans are replaced with 5-fluoro-L-tryptophan.

In some embodiments, the isolated polypeptide molecule is a fragment, unnatural analogue of wtGBP, or an unnatural analogue fragment of wtGBP, wherein one or more amino acids have been added to the N-terminus and/or the C-terminus of the isolated polypeptide molecule. For example, in some embodiments, Met-Arg can be added to the N-terminus of the isolated polypeptide molecule. For another example, in some embodiments, Arg-Ser-His-His-His-His-His-His can be added to the C-terminus of the isolated polypeptide molecule.

The presently-disclosed subject matter includes a biosensor capable of detecting glucose. As used herein, the term "detect" means to determine quantitatively and/or qualitatively. The biosensor includes an isolated polypeptide molecule that is capable of selectively binding glucose, and a label capable of generating a signal when the isolated polypeptide molecule binds glucose. The isolated polypeptide molecule of the biosensor can be an isolated polypeptide molecule as described above. The label can be associated with a binding site of the isolated polypeptide molecule, which label is capable of generating a signal. For example, the label can be a fluorescent label, e.g., fluorophore, or an electrochemical label.

As used herein, the terms "label" and "labeled" refer to the attachment of a moiety, capable of detection by spectroscopic, radiologic, or other methods, to a probe molecule. Thus, the terms "label" or "labeled" refer to incorporation or attachment, optionally covalently or non-covalently, of a detectable marker into a molecule, such as a polypeptide. Various methods of labeling polypeptides are known in the art and can be used. Specific examples are described herein. Fluorescent probes that can be utilized include, but are not limited to fluorescein isothiocyanate; fluorescein dichlorotriazine and fluorinated analogs of fluorescein; naphthofluorescein carboxylic acid and its succinimidyl ester; carboxyrhodamine 6G; pyridyloxazole derivatives; Cy2, 3, 3.5, 5, 5.5, and 7; phycoerythrin; phycoerythrin-Cy conjugates; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives (e.g., hydroxycoumarin, aminocoumarin, and methoxycoumarin); pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diaza-s-indacene; ALEXA FLUORS® (e.g., 350, 430,488, 532, 546, 555, 568, 594, 633, 647, 660, 680, 700, and 750); green fluorescent protein; yellow fluorescent protein; and fruit fluorescent proteins. The peak excitation and emission wavelengths will vary for these compounds and selection of a particular fluorescent probe for a particular application can be made in part based on excitation and/or emission wavelengths.

In some embodiments, the isolated polypeptide molecule is a fragment, an unnatural analogue, or an unnatural analogue fragment of a wtGBP; and the label is attached to an amino acid residue of the isolated polypeptide molecule. The label can be attached to one of the following amino acid sites close to the binding site of the isolated polypeptide molecule, and identified with reference to wtGBP of SEQ ID NO: 1: Asp 13, Asp 44, Val 68, Ala 71, Phe 90, Lys 92, Glu 93, Pro 94, Lys 97, Gly 109, Thr 110, Asp 111, Gly 151, Pro 153, Ala 155, Asp 184, Asp 212, Leu 255, Ala 258, Asn 260, Ala 262, Arg 292, Val 293, and Pro 294. The label can be a fluorophore, such as a fluorophore selected from: BODIPY 630/650 (Bromomethyl); ALEXA FLUORS® 680 679/702 (Maleimide); NBD 478/541 (Haloacetamide); PyMPO 415/570 (Haloacetamide); Texas Red 595/615 (Maleimide); and MDCC (N-[2-(1-maleimidyl(ethyl]-7-(diethylamino)coumarin-3-carboxamide).

The biosensors of the presently-disclosed subject matter can be utilized in a number of different capacities in order to detect glucose, both in vitro and in vivo. As one non-limiting example, the biosensor can be coupled with a catheter for continuous in vivo detection of glucose in a body of a subject. Any known catheter suitable for implantation in a body can be utilized with the biosensors disclosed herein, including but not limited to catheter systems disclosed in International Patent Application No. PCT/US08/732338 to Daunert et al. entitled "DEVICE FOR DETECTION OF MOLECULES OF INTEREST," claiming priority from U.S. Provisional Application Ser. Nos. 60/954,269 and 60/954,348, and filed on Aug. 6, 2008 (hereinafter referred to as the "Daunert et al. Application), which is incorporated herein by reference in its entirety.

In addition to coupling with catheter systems, the biosensors disclosed herein can also be utilized in several other systems for glucose detection. The incorporation of non-natural amino acids into single locations within glucose recognition peptides can allow for site-specific labeling with fluorophores, electrochemical tags, etc., due to the enhanced functional diversity that non-natural amino acids have in comparison to their canonical counterparts. This site specific potential provides for greater control and analytical reproducibility when developing glucose biosensors with non-natural glucose recognition peptides. The incorporation of non-natural amino acids further permits for the site-specific immobilization of these glucose recognition peptides, which can decrease the activity loss that is commonly encountered upon peptide immobilization. The retention of this glucose responsive activity can be useful in optimizing both hydrogel-catheter based glucose sensors disclosed in the Daunert et al. Application and in developing alternative sensor designs.

For example, the biosensors disclosed herein comprising novel glucose recognition peptides can be employed for the development of sensing systems on non-catheter platform systems. For example, the biosensors disclosed herein can be used to quantitate glucose levels on both microtiter plate and miniaturized microfluidics platforms, which are popular in high-throughput screening, clinical laboratory practice, and in the development of point-of-care diagnostic equipment. Additionally, presently-disclosed biosensors can be immobilized on affordable and robust paper strips, whose visible color change would correlate to glucose levels. These paper strips would be a practical and competitive option for patient self-monitoring of glucose levels. Moreover, the dynamic range of the glucose recognition peptides of the presently-disclosed subject matter can permit salivary analysis of glucose levels, instead of the painful and invasive finger prick method commonly used today.

In addition, the non-natural glucose recognition peptides disclosed herein and contained within hydrogel, as disclosed for example in the Daunert et al. Application can also be used for the development and improvement implantable drug delivery devices and contact lens glucose sensors. As an example of a potential use in implantable drug delivery devices, the change in fluorescent or electrical signal caused by glucose binding to the appropriately labeled glucose recognition peptides can be translated to the opening and closing of a reversible insulin-containing drug reservoir. In this manner glucose levels can be both monitored and corrected in diabetic patients with a glucose responsive glucose recognition peptide-hydrogel derived device. Additionally, current contact lens glucose sensors have a sensing plastic chip incorporated into the regular corrective lens. This plastic chip changes colors via holographic sensing methods and boron-containing fluorophores. These color changes are visible to the wearer, with different colors corresponding to different glucose levels in tears, thus alerting the patient if insulin is needed. One advantage the biosensors described herein have over this current contact lens scheme is that the glucose sensor disclosed herein can be hydrogel based. Hydrogels are more water and oxygen permeable than the plastic chips that are currently used, and this permeability is quite important for both the comfort and long term optical health of the contact lens wearer.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Expression and Labeling of Isolated Polypeptide Molecules. In order to obtain the gene for insertion into an expression vector, PCR amplification was employed. Primers were designed to amplify isolated polypeptide molecules of interest, e.g., polypeptide molecules of SEQ ID NOS: 1-7, and a fragment including amino acids 87-271 of SEQ ID NO: 1. Table B shows data from the fragment containing amino acids 87-271 from *E. coli*. This fragment showed large error and no clear trend in response to glucose, which demonstrates that rational design of truncated forms of wtGBPs is necessary to render a responsive glucose recognition peptide.

TABLE B

| Glucose Concentration (M) | Fluorescence Intensity (AVG) | Standard Deviation |
|---|---|---|
| 0 | 485.282 | 17.004 |
| 1.00E−08 | 442.682 | 32.888 |
| 1.00E−07 | 463.041 | 20.018 |
| 1.00E−06 | 497.146 | 22.400 |
| 1.00E−05 | 478.877 | 36.678 |
| 1.00E−04 | 467.383 | 41.020 |
| 1.00E−03 | 468.792 | 23.450 |

TABLE C

| Fluorescence signal quenching in response to varying concentration of glucose obtained from tGBPs. | | |
|---|---|---|
| | Percent Fluorescence Quenching | |
| Glucose, M | tGBP1 | tGBP2 |
| $1 \times 10^{-6}$ | −0.09539 | 1.748188 |
| $1 \times 10^{-5}$ | 2.907571 | 2.794934 |
| $1 \times 10^{-4}$ | 2.432862 | 5.87441 |
| $1 \times 10^{-3}$ | 7.5538 | 8.966095 |
| $1 \times 10^{-2}$ | 14.60875 | 7.50211 |
| $1 \times 10^{-1}$ | 20.36978 | 6.265703 |

Once the PCR amplified gene fragments were obtained, they were inserted into expression vector pQE70. The constructed expression plasmids were then transformed into the auxotrophic strain of *E. coli*. Protein expression was performed using medium shift method. A single freshly transformed colony was used to inoculate 5 mL of M9 media supplemented with 0.4% glucose; 1 mM MgSO$_4$; 0.1 mM CaCl$_2$; 1 mM Thiamine; 0.1 volume of a solution containing 0.01% (w/v) each of 20 amino acids, less any amino acid that is to be replaced by unnatural amino acids (e.g., each of 19 amino acids where one is to be replaced); 40 µg/mL of the remaining amino acid(s) (e.g., 20$^{th}$ amino acid), and appropriate amount of antibiotic. This culture was allowed to grow overnight at 37° C., 250 rpm. 500 mL culture containing the same ingredients was inoculated with the overnight grown 5 mL culture. This culture was then grown until the optical density (OD$_{600}$) was about 0.5. The cells were then centrifuged at 10000 rpm for 10 min, 25° C., the supernatant was discarded and the cells were resuspended in a 0.9% NaCl solution for washing, and this was repeated three times. The cells were then resuspended in 500 mL M9 minimal media which was supplemented with 0.4% glucose, 1 mM MgSO$_4$, 0.1 mM CaCl$_2$, 1 mM Thiamine, 0.1 volume of a solution containing 0.01% (w/v) each of 20 amino acids less any amino acid(s) to be replaced by unnatural amino acids (e.g., 19 amino acids), appropriate amount of antibiotic, and grown at 37° C. for 30 min to further deplete natural amino acid that has to be replaced by the unnatural amino acid. 1 mM IPTG was then added with 0.1 mM of unnatural amino acid to the culture and was grown overnight at 37° C. The cells were harvested by centrifugation and the protein was purified using Ni-NTA resin since GBP mutant has His-tag. The purified protein was then labeled with fluorophore MDCC (N-[2-(1-maleimidyl(ethyl]-7-(diethylamino)coumarin-3-carboxamide), e.g., labeled at cysteine-152 of SEQ ID NO: 1.

Fragments of wtGBP in Response to Glucose. In order to check for activity of the labeled tGBPs, an assay was performed. Upon glucose binding, the proteins should undergo a conformational change, resulting in a change in the local environment of the fluorophore molecule, which leads to a change in the fluorescence signal observed. The assay was carried out by preparing glucose solutions of concentrations ranging from $1 \times 10^{-1}$M to $1 \times 10^{-6}$M. These glucose standards were then added to 180 µL samples of the labeled tGBPs at a concentration of $1 \times 10^{-7}$M. The resulting fluorescence intensity was measured. The results obtained from one study including the isolated polypeptide molecules of SEQ ID NO: 2 (tGBP1) and SEQ ID NO: 3 (tGBP2) are presented in Table C.

Unnatural Analogues of wtGBP with Unnatural Tryptophans. Unnatural analogues of wtGBP from *E. coli* were produced, where natural tryptophans were replaced with unnatural tryptophans. Tryptophan auxotrophic strain of *E. coli* (#27873) was obtained. Plasmid placI and plasmid pQE70 containing the genetic sequence of the wtGBP mutated at 152 (containing a cysteine in this position for fluorophore attachment) were transformed into the tryptophan auxotrophic strain of *E. coli*. Protein expression was performed using medium shift method. A single freshly transformed colony was used to inoculate 5 mL of M9 media supplemented with 0.4% glucose, 1 mM MgSO$_4$, 0.1 mM CaCl$_2$, 1 mM Thiamine, 0.1 volume of a solution containing 0.01% (w/v) each of 18 amino acids (less Trp and Leu), 40 µg/mL Leu, 40 µg/mL Trp, 100 µg/mL Ampicillin, and 35 µg/mL Chloramphenicol.

This culture was allowed to grow overnight at 37° C., 250 rpm. 500 mL culture containing the same ingredients was inoculated with the overnight grown 5 mL culture. This culture was then grown till the optical density (OD$_{600}$) was about 0.5. The cells were then centrifuged at 10000 rpm for 10 min, 25° C., the supernatant was discarded and the cells were resuspended in a 0.9% NaCl solution for washing, and this was repeated three times. The cells were then resuspended in 500 mL M9 minimal media which was supplemented with 0.4% glucose, 1 mM MgSO$_4$, 0.1 mM CaCl$_2$, 1 mM Thiamine, 0.1 volume of a solution containing 0.01% (w/v) each of 18 amino acids (less Trp and Leu), 40 µg/mL Leu, 100 µg/mL Ampicillin and 35 µg/mL Chloramphenicol, and grown at 37° C. for 30 min to further deplete natural tryptophan. 1 mM IPTG was then added with 0.1 mM 5-Fluorotryptophan to the culture and was grown overnight at 37° C. The cells were harvested by centrifugation and the protein was purified using Ni-NTA resin since the produced mutant has a His-tag. The purified protein was then labeled with fluorophore MDCC (N-[2-(1-maleimidyl)ethyl]-7-(diethylamino)coumarin-3-carboxamide).

Unnatural Analogues of wtGBP with Unnatural Leucines. Unnatural analogues of wtGBP from *E. coli* were produced, where natural leucines were replaced with unnatural leucines. Leucine auxotrophic strain of *E. coli* HB101F was used for growing the glucose recognition protein with unnatural leucines. The procedure for growing and harvesting the cells was similar to the procedure described above with reference to unnatural analogues with unnatural tryptophans, except that no Chloramphenicol was added to the cultures.

Unnatural Analogues of wtGBP in Response to Glucose. Labeled protein was diluted to $5 \times 10^{-7}$ M and 180 µL of this diluted labeled protein was incubated with 20 µL of different concentrations of glucose ($10^{-2}$ M–$10^{-8}$ M) for 15 min at room temperature. Fluorescence of the samples was then measured using a Carry Eclipse Fluorimeter.

Figure 3:
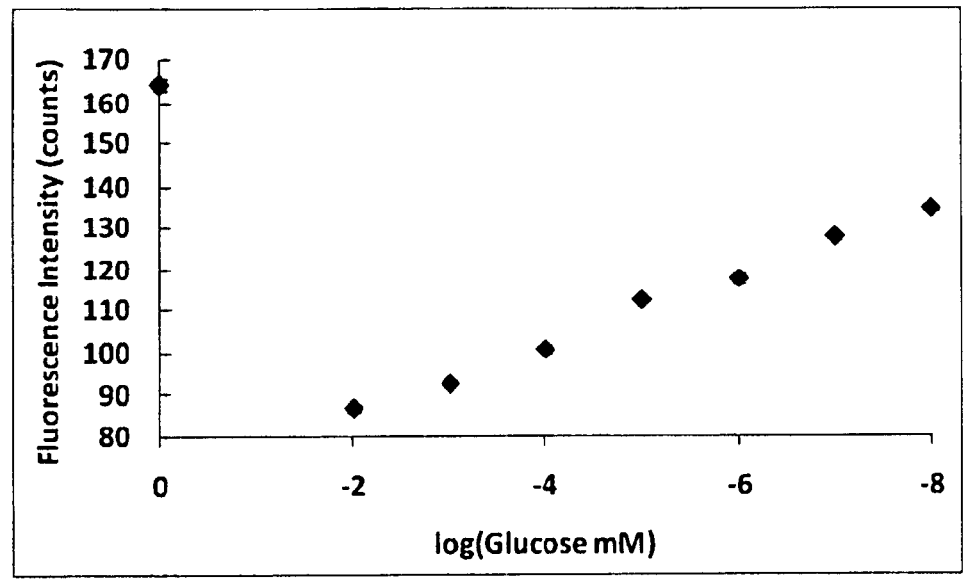
FIG. 3 is a dose response curve for glucose with an unnatural analogue of a wtGBP, including the isolated polypeptide of SEQ ID NO: 1, where natural tryptophans are replaced with 5-fluorotryptophans.

FIG. 3 is a dose response curve for glucose with an unnatural analogue of a wtGBP including unnatural tryptophan. The unnatural analogue of wtGBP is the isolated polypeptide of SEQ ID NO: 1, where all natural tryptophans are replaced with 5-fluorotryptophans. A dose-dependent change in fluorescence intensities observed when the unnatural analogue is contacted with increasing concentrations of glucose.

Figure 4:
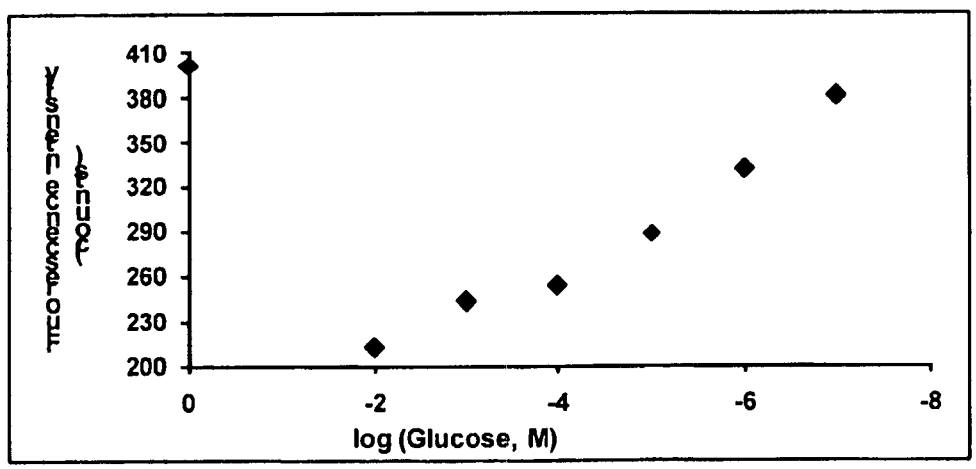
FIG. 4 is a dose response curve for glucose with an unnatural analogue fragment of a wtGBP, including the isolated polypeptide of SEQ ID NO: 2, where natural tryptophans are replaced with 5-fluorotryptophans.

FIG. 4 is a dose response curve for glucose with an unnatural analogue fragment of a wtGBP including unnatural tryptophan. The unnatural analogue fragment of wtGBP is the isolated polypeptide of SEQ ID NO: 2, where all natural tryptophans are replaced with 5-fluorotryptophans. A dose-dependent change in fluorescence intensities observed when the unnatural analogue fragment is contacted with increasing concentrations of glucose.

Figure 5:
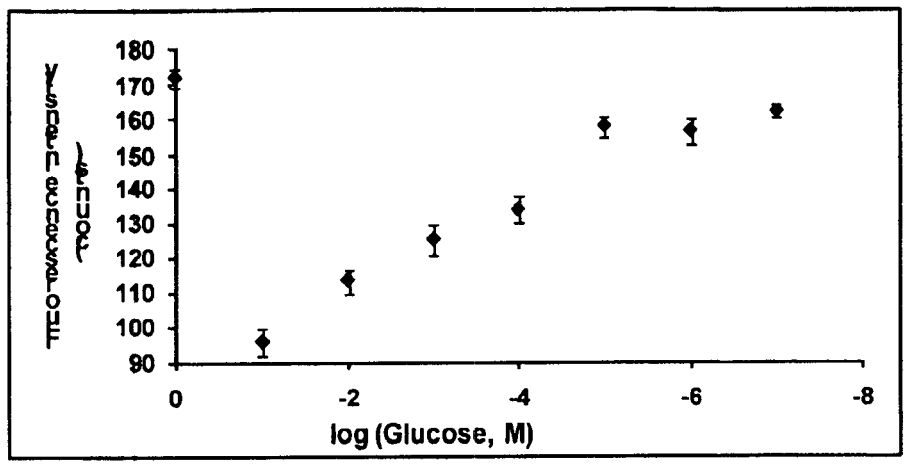
FIG. 5 is a dose response curve for glucose with an unnatural analogue fragment of a wtGBP, including the isolated polypeptide of SEQ ID NO: 3, where natural tryptophans are replaced with 5-fluorotryptophans.

FIG. 5 is a dose response curve for glucose with an unnatural analogue fragment of a wtGBP including unnatural tryptophan. The unnatural analogue fragment of wtGBP is the isolated polypeptide of SEQ ID NO: 3, where all natural tryptophans are replaced with 5-fluorotryptophans. A dose-dependent change in fluorescence intensities observed when the unnatural analogue fragment is contacted with increasing concentrations of glucose.

Figure 6:
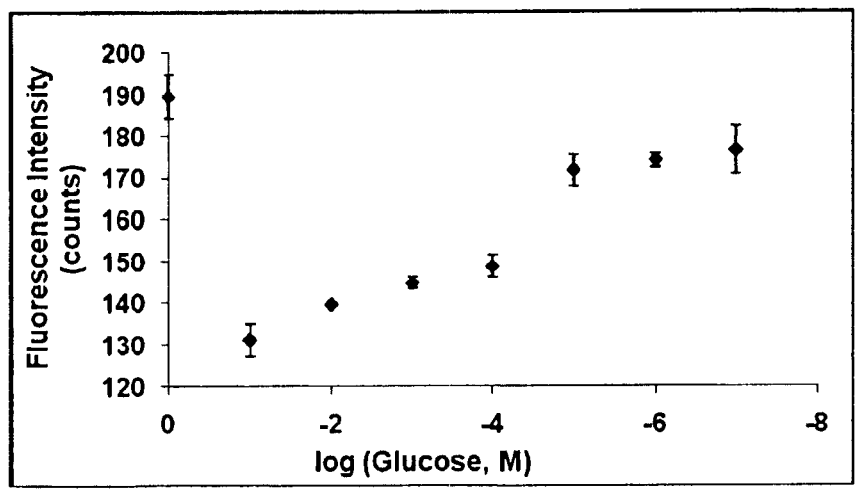
FIG. 6 is a dose response curve for glucose with an unnatural analogue of a wtGBP, including the isolated polypeptide of SEQ ID NO: 1, where natural leucines are replaced with 5,5,5-trifluoroleucines.

FIG. 6 is a dose response curve for glucose with an unnatural analogue of a wtGBP including unnatural leucine. The unnatural analogue of wtGBP is the isolated polypeptide of SEQ ID NO: 1, where all natural leucines are replaced with 5,5,5-trifluoroleucines. A dose-dependent change in fluorescence intensities observed when the unnatural analogue is contacted with increasing concentrations of glucose.

Figure 7:
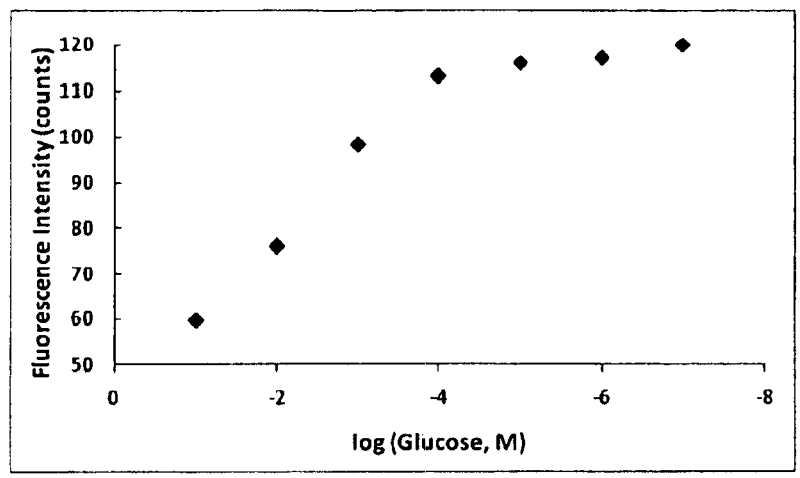
FIG. 7 is a dose response curve for glucose with an unnatural analogue fragment of a wtGBP, including the isolated polypeptide of SEQ ID NO: 2, where natural leucines are replaced with 5,5,5-trifluoroleucines.

FIG. 7 is a dose response curve for glucose with an unnatural analogue fragment of a wtGBP including unnatural leucine. The unnatural analogue fragment of wtGBP is the isolated polypeptide of SEQ ID NO: 2, where all natural leucines are replaced with 5,5,5-trifluoroleucines. A dose-dependent change in fluorescence intensities observed when the unnatural analogue fragment is contacted with increasing concentrations of glucose.

Figure 8:
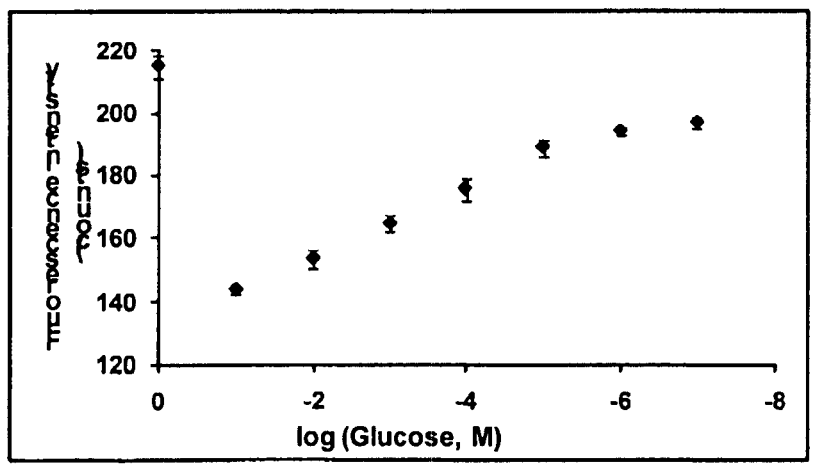
FIG. 8 is a dose response curve for glucose with an unnatural analogue fragment of a wtGBP, including the isolated polypeptide of SEQ ID NO: 3, where natural leucines are replaced with 5,5,5-trifluoroleucines.

FIG. 8 is a dose response curve for glucose with an unnatural analogue fragment of a wtGBP including unnatural leucine. The unnatural analogue fragment of a wtGBP is the isolated polypeptide of SEQ ID NO: 3, where all natural leucines are replaced with 5,5,5-trifluoroleucines. A dose-dependent change in fluorescence intensities observed when the unnatural analogue fragment is contacted with increasing concentrations of glucose.

Figure 9:
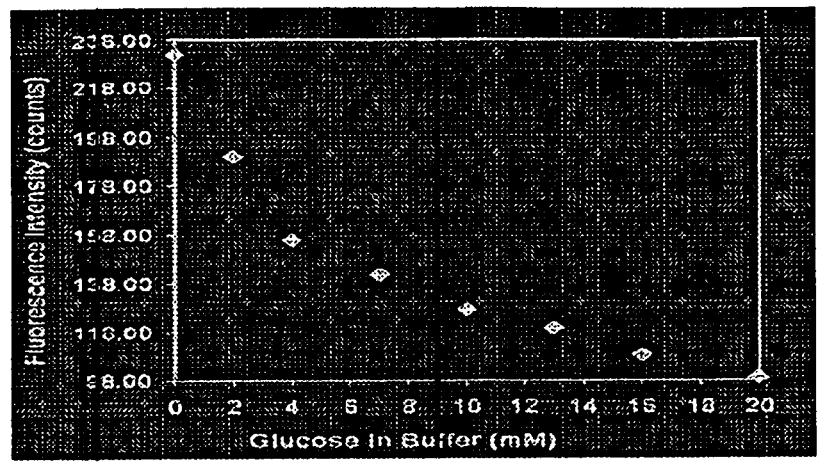
FIG. 9 is a dose response curve for glucose with an unnatural analogue of wtGBP including unnatural tryptophan, immobilized on a fiber optic tip.

Labeled protein was immobilized in an acrylamide based hydrogel and the hydrogel was then immobilized on the tip of an optical fiber. The tip of the optical fiber with immobilized hydrogel was then dipped in glucose solutions of different concentration made in 10 mM HEPES, 0.2 mM $CaCl_2$, pH 8.0 buffer and the change in fluorescence intensity was measured using an Ocean Optics fiber optic instrument. FIG. 9 is a dose response curve for glucose in buffer with an unnatural analogue of wtGBP including unnatural tryptophan, immobilized on a fiber optic tip. A dose-dependent change in fluorescence intensities observed when the unnatural analogue fragment is contacted with increasing concentrations of glucose.

Figure 10:
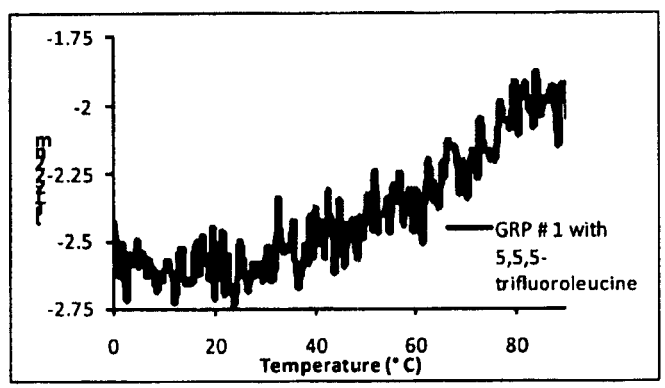
FIG. 10 is a circular dichroism (CD) spectrum of an unnatural analogue of a wtGBP, including the isolated polypeptide of SEQ ID NO: 2, where natural leucines are replaced with 5,5,5-trifluoroleucines.
Figure 11:
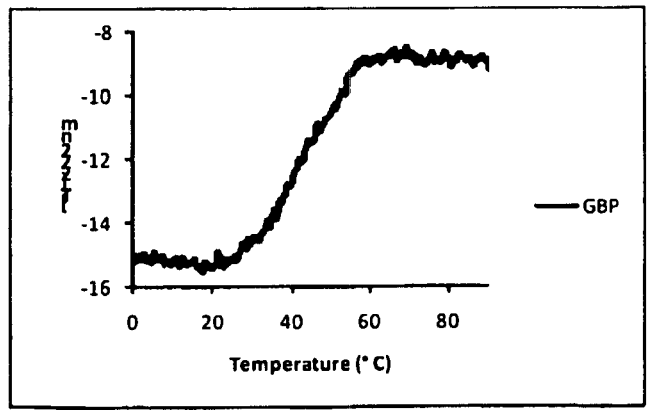
FIG. 11 is a CD spectrum of a wtGBP, including the isolated polypeptide of SEQ ID NO: 1.

Circular dichroism (CD) spectra were obtained to determine the structural integrity at different temperatures, i.e., thermal stability, of an unnatural analogue fragment of a wtGBP including unnatural leucines, as compared to a wtGBP. FIG. 10 is a circular dichroism spectrum of an unnatural analogue fragment of a wtGBP. The unnatural analogue of wtGBP is the isolated polypeptide of SEQ ID NO: 2, where all natural leucines are replaced with 5,5,5-trifluoroleucines. FIG. 11 is a CD spectrum of a wtGBP, including the isolated polypeptide of SEQ ID NO: 1. The CD spectrum of FIG. 11 shows that the wtGBP is stable within the temperature range of about 35° C. to about 55° C. The CD spectrum of FIG. 10 shows that the unnatural analogue including unnatural leucines has better thermal stability, showing stability over a wider range of about 35° C. to about 75° C.

Method of Detecting Molecules of Interest

An exemplary method for continuous detection of a molecule of interest includes initially immersing a tip of an optical fiber having a biosensor positioned on said tip into a sample. The biosensor includes an isolated peptide having a binding site that selectively binds said molecule of interest. Upon binding the molecule of interest, the peptide emits a signal that is transmitted by said optical fiber, to thereby detect said molecule of interest. The method further includes collecting the signal with a detection and data collection device operably connected with the optical fiber and then correlating the signal to an amount of the molecule of interest. The amount of the molecule of interest can then be displayed. In some embodiments, the molecule of interest can be glucose or IL-6, and the biosensor peptide can be a glucose binding protein or an IL-6-specific antibody, respectively.

In this exemplary embodiment, the peptide has high stability at physiological conditions and is incorporated within an optically transparent hydrogel positioned on said distal tip. The biosensor includes a label associated with the binding site. The label generates the signal and is selected from a fluorescent label and an electrochemical label.

When the molecule of interest is glucose, the hydrogel can include a precursor solution of bisacrylamide, acrylamide, buffer solution, glycerol, glucose binding protein, acrylic acid, and 2,2-Diethoxyacetaphenone. The precursor solution can be UV polymerized for approximately 30 minutes to form the hydrogel incorporated with the peptide.

Finally, the sample can be a blood stream or body fluid in a body of a subject, in vivo, or can be an in vitro sample.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A biosensor for detecting a molecule of interest, comprising:
   an isolated polypeptide molecule capable of selectively-binding glucose, wherein the polypeptide molecule is selected from: an unnatural analogue of the amino acid sequence of SEQ ID NO: 2; and an unnatural analogue fragment of the amino acid sequence of SEQ ID NO: 2; and
   a label associated with the polypeptide molecule;
   wherein binding of glucose to the polypeptide molecule causes the label to generate a signal, such that the glucose can be detected.

2. The biosensor of claim 1, wherein the polypeptide molecule is an unnatural analogue fragment of the amino acid sequence of SEQ ID NO: 2.

3. The biosensor of claim 1, wherein the polypeptide molecule comprises the amino acid sequence of SEQ ID NO: 2, wherein one or more natural amino acids are replaced with one or more unnatural amino acids.

4. The biosensor of claim 1, wherein one or more natural amino acids of the unnatural analogue or unnatural analogue fragment are replaced with one or more unnatural amino acids as set forth in Table A.

5. The biosensor of claim 4, wherein one or more natural leucines are replaced with 5,5,5-trifluoroleucine.

6. The biosensor of claim 4, wherein one or more natural tryptophans are replaced with 5-fluorotryptophan.

7. The biosensor of claim 4, wherein one or more natural leucines are replaced with 5,5,5-trifluoro-DL-leucine.

8. The biosensor of claim 4, wherein one or more natural tryptophans are replaced with 5-fluoro-L-tryptophan.

9. The biosensor of claim 1, wherein the polypeptide molecule comprises the amino acid sequence of SEQ ID NO: 2, wherein one or more natural leucines are replaced with 5,5,5-trifluoroleucine.

10. The biosensor of claim 1, wherein the polypeptide molecule comprises the amino acid sequence of SEQ ID NO: 2, wherein one or more natural tryptophans are replaced with 5-fluorotryptophan.

11. The biosensor of claim 1, wherein the polypeptide molecule is stable over a wider range of temperatures relative to wild type GBP (wtGBP).

12. The biosensor of claim 1, wherein the polypeptide molecule is stable at temperatures between about 55° C. and about 75° C.

13. The biosensor of claim 12, wherein the polypeptide molecule is an unnatural analogue or an unnatural analogue fragment, wherein one or more natural leucines are replaced with unnatural leucines.

14. The biosensor of claim 13, wherein the unnatural leucines are 5,5,5-trifluoroleucine.

15. The biosensor of claim 1, wherein the label is a fluorophore.

16. The biosensor of claim 15, wherein the polypeptide molecule comprises: an unnatural analogue of the amino acid sequence of SEQ ID NO: 2; or an unnatural analogue fragment of the amino acid sequence of SEQ ID NO: 2; wherein the label is attached to an amino acid site of the polypeptide molecule selected from Asp 44, Val 68, Ala 71, Phe 90, Lys 92, Glu 93, Pro 94, Lys 97, Gly 109, Thr 110, Asp 111, Gly 151, Cys 152, Pro 153, Ala 155, Asp 184, Asp 212, Leu 255, Ala 258, Asn 260, Ala 262, Arg 292, Val 293, and Pro 294, wherein SEQ ID NO: 2 comprises amino acids numbered 14-296 of wild type GBP (wtGBP).

17. The biosensor of claim 16, wherein label is the fluorophore N-[2-(1-maleimidyl(ethyl]-7-(diethylamino)coumarin-3-carboxamide (MDCC).

18. The biosensor of claim 16, wherein binding of glucose to the polypeptide molecule causes the label to generate a detectably altered fluorescence intensity of the fluorophore such that the glucose can be detected.

19. The biosensor of claim 18, wherein the fluorescence intensity can be correlated to the concentration of the glucose in a sample.

20. A method for detecting a glucose, comprising:
contacting the biosensor of claim 1 with a sample of interest;
detecting the signal; and
collecting and displaying the signal with a detection and data collection device, to thereby detect the glucose.

21. The method of claim 20, wherein the glucose is continuously detected.

22. An isolated polypeptide molecule capable of selectively-binding glucose, wherein the polypeptide molecule is selected from an unnatural analogue of the amino acid sequence of SEQ ID NO: 2; and an unnatural analogue fragment of the amino acid sequence of SEQ ID NO: 2.

* * * * *

SEQUENCE LISTING

<160> NUMBER OF SEQ ID NOS: 4

<210> SEQ ID NO 1
<211> LENGTH: 309
<212> TYPE: PRT
<213> ORGANISM: E. Coli

<400> SEQUENCE: 1

Leu Asp Thr Arg Ile Gly Val Thr Ile Tyr Lys Tyr Asp Asp Asn Phe
1               5                   10                  15

Met Ser Val Val Arg Lys Ala Ile Glu Gln Asp Ala Lys Ala Ala Pro
            20                  25                  30

Asp Val Gln Leu Leu Met Asn Asp Ser Gln Asn Asp Ser Lys Gln
        35                  40                  45

Asn Asp Gln Ile Asp Val Leu Leu Ala Lys Gly Val Lys Ala Leu Ala
    50                  55                  60

Ile Asn Leu Val Asp Pro Ala Ala Ala Gly Thr Val Ile Glu Lys Ala
65                  70                  75                  80

Arg Gly Gln Asn Val Pro Val Phe Phe Asn Lys Glu Pro Ser Arg
                85                  90                  95

Lys Ala Leu Asp Ser Tyr Asp Lys Ala Tyr Tyr Val Gly Thr Asp Ser
            100                 105                 110

Lys Glu Ser Gly Ile Ile Gln Gly Asp Leu Ile Ala Lys His Trp Ala
            115                 120                 125

Ala Asn Gln Gly Trp Asp Leu Asn Lys Asp Gly Gln Ile Gln Phe Val
    130                 135                 140

Leu Leu Lys Gly Glu Pro Gly Cys Pro Asp Ala Glu Ala Arg Thr Thr
145                 150                 155                 160

Tyr Val Ile Lys Glu Leu Asn Asp Lys Gly Ile Lys Thr Glu Gln Leu
                165                 170                 175

Gln Leu Asp Thr Ala Met Trp Asp Thr Ala Gln Ala Lys Asp Lys Met
            180                 185                 190

Asp Ala Trp Leu Ser Gly Pro Asn Ala Asn Lys Ile Glu Val Val Ile
    195                 200                 205

Ala Asn Asn Asp Ala Met Ala Met Gly Ala Val Glu Ala Leu Lys Ala
    210                 215                 220

His Asn Lys Ser Ser Ile Pro Val Phe Gly Val Asp Ala Leu Pro Glu
225                 230                 235                 240

Ala Leu Ala Leu Val Lys Ser Gly Ala Leu Ala Gly Thr Val Leu Asn
                245                 250                 255

Asp Ala Asn Asn Gln Ala Lys Ala Thr Phe Asp Leu Ala Lys Asn Leu
            260                 265                 270

Ala Asp Gly Lys Gly Ala Ala Asp Gly Thr Asn Trp Lys Ile Asp Asn
        275                 280                 285

Lys Val Val Arg Val Pro Tyr Val Gly Val Asp Lys Asp Asn Leu Ala
    290                 295                 300

Glu Phe Ser Lys Lys
305

<210> SEQ ID NO 2
<211> LENGTH: 283
<212> TYPE: PRT
<213> ORGANISM: E. Coli

<400> SEQUENCE: 2

Asp Asn Phe Met Ser Val Val Arg Lys Ala Ile Glu Gln Asp Ala Lys
1               5                   10                  15

Ala Ala Pro Asp Val Gln Leu Leu Met Asn Asp Ser Gln Asn Asp Gln
            20                  25                  30

Ser Lys Gln Asn Asp Gln Ile Asp Val Leu Leu Ala Lys Gly Val Lys
        35                  40                  45

Ala Leu Ala Ile Asn Leu Val Asp Pro Ala Ala Ala Gly Thr Val Ile
    50                  55                  60

```
Glu Lys Ala Arg Gly Gln Asn Val Pro Val Val Phe Phe Asn Lys Glu
 65                  70                  75                  80

Pro Ser Arg Lys Ala Leu Asp Ser Tyr Asp Lys Ala Tyr Tyr Val Gly
                 85                  90                  95

Thr Asp Ser Lys Glu Ser Gly Ile Ile Gln Gly Asp Leu Ile Ala Lys
            100                 105                 110

His Trp Ala Ala Asn Gly Trp Asp Leu Asn Lys Asp Gly Gln Ile
            115                 120                 125

Gln Phe Val Leu Leu Lys Gly Glu Pro Gly His Pro Asp Ala Glu Ala
        130                 135                 140

Arg Thr Thr Tyr Val Ile Lys Glu Leu Asn Asp Lys Gly Ile Lys Thr
145                 150                 155                 160

Glu Gln Leu Gln Leu Asp Thr Ala Met Trp Asp Thr Ala Gln Ala Lys
                165                 170                 175

Asp Lys Met Asp Ala Trp Leu Ser Gly Pro Asn Ala Asn Lys Ile Glu
            180                 185                 190

Val Val Ile Ala Asn Asn Asp Ala Met Ala Met Gly Ala Val Glu Ala
            195                 200                 205

Leu Lys Ala His Asn Lys Ser Ser Ile Pro Val Phe Gly Val Asp Ala
        210                 215                 220

Leu Pro Glu Ala Leu Ala Leu Val Lys Ser Gly Ala Leu Ala Gly Thr
225                 230                 235                 240

Val Leu Asn Asp Ala Asn Asn Gln Ala Lys Ala Thr Phe Asp Leu Ala
            245                 250                 255

Lys Asn Leu Ala Asp Gly Lys Gly Ala Ala Asp Gly Thr Asn Trp Lys
            260                 265                 270

Ile Asp Asn Lys Val Val Arg Val Pro Tyr Val
            275                 280

<210> SEQ ID NO 3
<211> LENGTH: 243
<212> TYPE: PRT
<213> ORGANISM: E. Coli

<400> SEQUENCE: 3

Asp Asn Phe Met Ser Val Val Arg Lys Ala Ile Glu Gln Asp Ala Lys
  1               5                  10                  15

Ala Ala Pro Asp Val Gln Leu Leu Met Asn Asp Ser Gln Asn Asp Gln
                 20                  25                  30

Ser Lys Gln Asn Asp Gln Ile Asp Val Leu Leu Ala Lys Gly Val Lys
            35                  40                  45

Ala Leu Ala Ile Asn Leu Val Asp Pro Ala Ala Ala Gly Thr Val Ile
        50                  55                  60

Glu Lys Ala Arg Gly Gln Asn Val Pro Val Val Phe Phe Asn Lys Glu
 65                  70                  75                  80

Pro Ser Arg Lys Ala Leu Asp Ser Tyr Asp Lys Ala Tyr Tyr Val Gly
                 85                  90                  95

Thr Asp Ser Lys Glu Ser Gly Ile Ile Gln Gly Asp Leu Ile Ala Lys
            100                 105                 110

His Trp Ala Ala Asn Gly Trp Asp Leu Asn Lys Asp Gly Gln Ile
            115                 120                 125

Gln Phe Val Leu Leu Lys Gly Glu Pro Gly His Pro Asp Ala Glu Ala
        130                 135                 140

Arg Thr Thr Tyr Val Ile Lys Glu Leu Asn Asp Lys Gly Ile Lys Thr
145                 150                 155                 160
```

```
Glu Gln Leu Gln Leu Asp Thr Ala Met Trp Asp Thr Ala Gln Ala Lys
                165                 170                 175

Asp Lys Met Asp Ala Trp Leu Ser Gly Pro Asn Ala Asn Lys Ile Glu
            180                 185                 190

Val Val Ile Ala Asn Asn Asp Ala Met Ala Met Gly Ala Val Glu Ala
        195                 200                 205

Leu Lys Ala His Asn Lys Ser Ser Ile Pro Val Phe Gly Val Asp Ala
    210                 215                 220

Leu Pro Glu Ala Leu Ala Leu Val Lys Ser Gly Ala Leu Ala Gly Thr
225                 230                 235                 240

Val Leu Asn

<210> SEQ ID NO 4
<211> LENGTH: 185
<212> TYPE: PRT
<213> ORGANISM: E. Coli

<400> SEQUENCE: 4

Val Val Phe Phe Asn Lys Glu Pro Ser Arg Lys Ala Leu Asp Ser Tyr
1               5                   10                  15

Asp Lys Ala Tyr Tyr Val Gly Thr Asp Ser Lys Glu Ser Gly Ile Ile
            20                  25                  30

Gln Gly Asp Leu Ile Ala Lys His Trp Ala Ala Asn Gln Gly Trp Asp
        35                  40                  45

Leu Asn Lys Asp Gly Gln Ile Gln Phe Val Leu Leu Lys Gly Glu Pro
    50                  55                  60

Gly His Pro Asp Ala Glu Ala Arg Thr Thr Tyr Val Ile Lys Glu Leu
65                  70                  75                  80

Asn Asp Lys Gly Ile Lys Thr Glu Gln Leu Gln Leu Asp Thr Ala Met
            85                  90                  95

Trp Asp Thr Ala Gln Ala Lys Asp Lys Met Asp Ala Trp Leu Ser Gly
        100                 105                 110

Pro Asn Ala Asn Lys Ile Glu Val Val Ile Ala Asn Asn Asp Ala Met
    115                 120                 125

Ala Met Gly Ala Val Glu Ala Leu Lys Ala His Asn Lys Ser Ser Ile
130                 135                 140

Pro Val Phe Gly Val Asp Ala Leu Pro Glu Ala Leu Ala Leu Val Lys
145                 150                 155                 160

Ser Gly Ala Leu Ala Gly Thr Val Leu Asn Asp Ala Asn Asn Gln Ala
            165                 170                 175

Lys Ala Thr Phe Asp Leu Ala Lys Asn
            180                 185
```